(12) United States Patent
Zhang et al.

(10) Patent No.: US 11,770,146 B2
(45) Date of Patent: Sep. 26, 2023

(54) APPARATUS AND METHOD FOR REMOVING HIGH-FREQUENCY RADIO FREQUENCY INTERFERENCE

(71) Applicants: SHENZHEN MINDRAY BIO-MEDICAL ELECTRONICS CO., LTD., Shenzhen (CN); Shenzhen Mindray Scientific Co., Ltd., Shenzhen (CN)

(72) Inventors: Peng Zhang, Shenzhen (CN); Ningling Zhang, Shenzhen (CN); Junhua Xie, Shenzhen (CN); Xingliang Jin, Shenzhen (CN); Xianliang He, Shenzhen (CN); Zhigang Ye, Shenzhen (CN); Hanyuan Luo, Shenzhen (CN); Ming Li, Shenzhen (CN); Zuming Yao, Shenzhen (CN)

(73) Assignees: SHENZHEN MINDRAY BIO-MEDICAL ELECTRONICS CO., LTD., Shenzhen (CN); SHENZHEN MINDRAY SCIENTIFIC CO., LTD., Shenzhen (CN)

( * ) Notice: Subject to any disclaimer, the term of this patent is extended or adjusted under 35 U.S.C. 154(b) by 454 days.

(21) Appl. No.: 16/916,050

(22) Filed: Jun. 29, 2020

(65) Prior Publication Data
US 2020/0336162 A1    Oct. 22, 2020

Related U.S. Application Data

(63) Continuation-in-part of application No. PCT/CN2017/120370, filed on Dec. 30, 2017.

(51) Int. Cl.
*H04B 1/10* (2006.01)
*A61B 5/00* (2006.01)
(Continued)

(52) U.S. Cl.
CPC .......... *H04B 1/1027* (2013.01); *A61B 5/316* (2021.01); *A61B 5/369* (2021.01); *A61B 5/7203* (2013.01)

(58) Field of Classification Search
CPC ....... H04B 1/1027; A61B 5/316; A61B 5/369; A61B 5/7203
See application file for complete search history.

(56) References Cited

U.S. PATENT DOCUMENTS 5,813,993 A * 9/1998 Kaplan ............... A61B 5/7203
600/26
6,175,762 B1 * 1/2001 Kirkup .................. A61B 5/375
600/544
(Continued)

FOREIGN PATENT DOCUMENTS

CN         1665443 A    9/2005
CN       101361652 A    2/2009
(Continued)

OTHER PUBLICATIONS

International Search Report issued in corresponding International Application No. PCT/CN2017/120370, dated Sep. 26, 2018, 4 pages.
(Continued)

*Primary Examiner* — Jinsong Hu
*Assistant Examiner* — Rui M Hu
(74) *Attorney, Agent, or Firm* — BAYES PLLC

(57) ABSTRACT

An apparatus and method for removing high-frequency radio frequency interference are disclosed. The apparatus includes a filtering unit for filtering an original electroencephalogram signal to obtain an intermediate electroencephalogram signal; a high-frequency signal extraction unit for filtering the intermediate electroencephalogram signal to extract a high-frequency signal from the intermediate electroencephalogram signal; a marking unit for comparing the
(Continued)

amplitude of the high-frequency signal with a comparison threshold value, and performing classification marking on the intermediate electroencephalogram signal according to a comparison result; a collection unit for sampling the intermediate electroencephalogram signal that has been performed with the classification marking to obtain a desired electroencephalogram signal and inputting the desired electroencephalogram signal into a processor; and the processor for setting the comparison threshold value and controlling the collection unit to perform sampling.

11 Claims, 5 Drawing Sheets

(51) Int. Cl.
*A61B 5/316* (2021.01)
*A61B 5/369* (2021.01)

(56) References Cited

U.S. PATENT DOCUMENTS

| | | | | |
|---|---|---|---|---|
| 7,403,820 | B2* | 7/2008 | DiLorenzo | A61N 1/3605 607/45 |
| 7,904,160 | B2* | 3/2011 | Brodnick | A61B 5/30 607/27 |
| 8,538,512 | B1* | 9/2013 | Bibian | A61B 5/4839 600/545 |
| 8,731,654 | B2* | 5/2014 | Johnson | A61G 13/10 600/382 |
| 9,610,016 | B2* | 4/2017 | Shusterman | A61B 5/318 |
| 10,194,821 | B2* | 2/2019 | Habte | A61B 5/352 |
| 10,376,167 | B2* | 8/2019 | Mahon | A61N 1/0456 |
| 10,751,524 | B2* | 8/2020 | Ridler | H04R 25/505 |
| 10,874,318 | B2* | 12/2020 | Shahdoostfard | A61B 5/305 |
| 11,406,303 | B2* | 8/2022 | Mahon | A61N 1/0456 |
| 2004/0208138 | A1* | 10/2004 | Hayashi | H04L 25/0232 370/286 |
| 2005/0234361 | A1* | 10/2005 | Holland | A61B 5/349 607/9 |
| 2006/0122525 | A1* | 6/2006 | Shusterman | A61B 5/6822 600/513 |
| 2007/0038382 | A1* | 2/2007 | Keenan | A61B 5/7257 600/509 |
| 2007/0135727 | A1* | 6/2007 | Virtanen | A61B 5/369 600/544 |
| 2007/0156063 | A1 | 7/2007 | Zoth et al. | |
| 2007/0167858 | A1* | 7/2007 | Virtanen | A61B 5/369 600/544 |
| 2008/0051844 | A1* | 2/2008 | Brodnick | A61B 5/30 607/27 |
| 2008/0094274 | A1* | 4/2008 | Nakanishi | G01S 7/023 342/91 |
| 2009/0124869 | A1* | 5/2009 | Hu | A61B 5/333 600/301 |
| 2009/0143693 | A1* | 6/2009 | Ye | A61B 5/7203 600/523 |
| 2009/0198498 | A1 | 8/2009 | Ramabadran et al. | |
| 2010/0030096 | A1* | 2/2010 | Bradley | A61B 5/38 600/544 |
| 2010/0168595 | A1* | 7/2010 | Lee | A61B 5/318 600/509 |
| 2010/0198099 | A1* | 8/2010 | Murphy | A61B 5/7217 600/546 |
| 2011/0066052 | A1* | 3/2011 | Mascarenhas | A61B 5/316 600/509 |
| 2011/0224570 | A1* | 9/2011 | Causevic | A61B 5/378 600/544 |
| 2012/0142364 | A1* | 6/2012 | Duan | H04W 52/244 455/450 |
| 2013/0338518 | A1* | 12/2013 | Zoica | A61B 5/7225 600/516 |
| 2014/0020089 | A1* | 1/2014 | Perini, II | G06F 21/32 726/19 |
| 2014/0276186 | A1* | 9/2014 | Stanslaski | A61B 5/30 600/300 |
| 2015/0061758 | A1* | 3/2015 | Hsu | A61B 5/30 327/556 |
| 2015/0283387 | A1* | 10/2015 | Sun | A61B 5/349 607/27 |
| 2015/0305642 | A1 | 10/2015 | Reinke et al. | |
| 2016/0007928 | A1* | 1/2016 | Chiu | A61B 5/7246 600/386 |
| 2016/0055415 | A1* | 2/2016 | Baxi | G16H 10/60 706/52 |
| 2016/0228018 | A1* | 8/2016 | Mahon | A61N 1/20 |
| 2018/0069578 | A1* | 3/2018 | Lee | H01Q 21/28 |
| 2018/0140203 | A1* | 5/2018 | Wang | A61B 5/11 |
| 2018/0253185 | A1* | 9/2018 | Imanilov | H04L 5/0021 |
| 2019/0159733 | A1* | 5/2019 | Shusterman | A61N 1/3718 |
| 2019/0306675 | A1* | 10/2019 | Xue | H04B 17/345 |
| 2019/0336723 | A1* | 11/2019 | Garcia Molina | A61B 5/369 |
| 2019/0357789 | A1* | 11/2019 | Mahon | A61B 5/311 |
| 2020/0337575 | A1* | 10/2020 | Amaya | A61B 5/7217 |
| 2022/0202341 | A1* | 6/2022 | Upadrashta | A61B 5/316 |
| 2022/0369996 | A1* | 11/2022 | Mahon | A61B 5/4041 |

FOREIGN PATENT DOCUMENTS

| | | |
|---|---|---|
| CN | 101869477 A | 10/2010 |
| CN | 103454949 A | 12/2013 |
| CN | 103610461 A | 3/2014 |
| CN | 103932701 A | 7/2014 |
| CN | 105030232 A | 11/2015 |
| CN | 105764413 A | 7/2016 |

OTHER PUBLICATIONS

First Office Action issued in Chinese Application No. 201780085029.6, dated Jul. 5, 2019, 12 pages.

* cited by examiner

APPARATUS AND METHOD FOR REMOVING HIGH-FREQUENCY RADIO FREQUENCY INTERFERENCE

CROSS-REFERENCE

This disclosure is a continuation-in-part of Patent Cooperation Treaty Application No. PCT/CN2017/120370, filed on Dec. 30, 2017, which is hereby incorporated by reference.

TECHNICAL FIELD

This disclosure relates to the technical field of medical equipment, and in particular to an apparatus and method for removing high-frequency radio frequency interference.

BACKGROUND

A high-frequency electrotome (a high-frequency scalpel) is an electrosurgical unit (ESU) that replaces a mechanical scalpel for tissue cutting. It can heat the contacted body through high-frequency and high-voltage signals generated by an effective electrode tip, and realize the separation and coagulation of the body tissue, so as to achieve the purpose of cutting and hemostasis. Now, it is more and more widely used in clinical surgery. However, the high-frequency signals generated by the electrotome have a great impact on physiological signals during surgery. This is a challenge of the current patient monitoring during surgery, and improper treatment will cause monitoring to be interrupted or provide wrong parameters, which affects the doctor's assessment of the conditions of a patient.

In a patient monitoring system, the current method for detecting ESU high-frequency interference mainly includes designing corresponding filters to remove the high-frequency interference signals based on frequency-domain distribution difference between interference signals and physiological signals, or providing interference signal marks based on the changes in the frequency-domain features. Frequency domain analysis requires Fourier transform of a signal, which is high in the calculation complexity, takes large resource occupation and large time consumption.

SUMMARY

In one aspect, this disclosure can provide an apparatus for removing high-frequency radio frequency interference, including: a filtering unit, a high-frequency signal extraction unit, a marking unit, a collection unit, and a processor.

The filtering unit may include an input port and an output port, where its input port may be inputted with an original electroencephalogram signal. The high-frequency signal extraction unit may include an input port and an output port, where its input port may be connected with the output port of the filtering unit. The collection unit may include an input port and an output port, where its input port may be connected with the output port of the filtering unit. The processor may include an input port and an output port, where its input port may be connected with the output port of the collection unit. The marking unit may include an input port that may be connected with the output port of the high-frequency signal extraction unit and the output port of the processor.

The filtering unit can be configured for filtering the original electroencephalogram signal to obtain an intermediate electroencephalogram signal. The high-frequency signal extraction unit can be configured for filtering the intermediate electroencephalogram signal to extract a high-frequency signal of the intermediate electroencephalogram signal. The marking unit can be configured for comparing an amplitude of the high-frequency signal with a comparison threshold value, and performing classification marking on the intermediate electroencephalogram signal when a comparison result indicates that the amplitude of the high-frequency signal is greater than the comparison threshold value. The collection unit can be configured for selectively sampling the intermediate electroencephalogram signal to obtain a desired electroencephalogram signal and inputting the desired electroencephalogram signal into the processor. The processor can be configured for setting the comparison threshold value used by the marking unit and controlling the collection unit to sample the intermediate electroencephalogram signal.

In another aspect, this disclosure may provide a method for removing high-frequency radio frequency interference. The method may include:

acquiring an electroencephalogram signal;

performing high-pass filtering on the electroencephalogram signal to obtain an intermediate signal;

obtaining a time-domain feature of the intermediate signal within a first preset duration, and obtaining a detection threshold value according to the time-domain feature;

obtaining a sub-intermediate signal within a second preset duration, and determining a signal type of the sub-intermediate signal according to the detection threshold value, wherein different signal types reflect different degrees of interference on the electroencephalogram signal; and performing, according to the determined signal type, corresponding processing on the electroencephalogram signal corresponding to the sub-intermediate signal.

In yet another aspect, this disclosure may provide an apparatus for removing high-frequency radio frequency interference, which may include:

a collection circuit that collects an electroencephalogram signal, and a processor that is configured for:

performing high-pass filtering on the electroencephalogram signal to obtain an intermediate signal;

obtaining a time-domain feature of the intermediate signal within a first preset duration, and obtaining a detection threshold value according to the time-domain feature;

obtaining a sub-intermediate signal within a second preset duration, and determining a signal type of the sub-intermediate signal according to the detection threshold value, wherein different signal types reflect different degrees of interference on the electroencephalogram signal; and performing, according to the determined signal type, corresponding processing on the electroencephalogram signal corresponding to the sub-intermediate signal.

In the embodiments of this disclosure, a detection threshold value of a high-frequency radio frequency interference signal is obtained by analyzing an electroencephalogram signal in a time domain, and the high-frequency radio frequency interference signal is detected according to the detection threshold value, such that classification processing can be performed on the electroencephalogram signal corresponding to the high-frequency radio frequency interference signal.

BRIEF DESCRIPTION OF THE DRAWINGS

Following detailed descriptions of respective embodiments in this disclosure can be understood better when combining with these figures, in which the same structure is represented by the same reference sign. In the figures.

DETAILED DESCRIPTION

Figure 1:
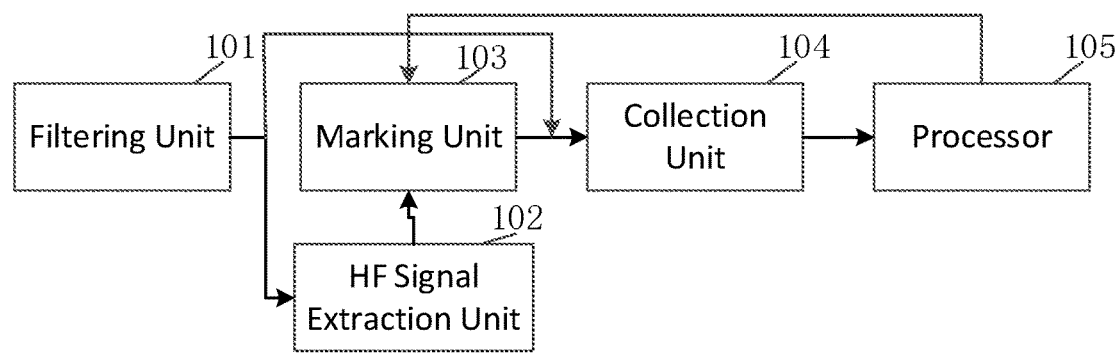
FIG. 1 is a block diagram for an apparatus for removing high-frequency radio frequency interference provided by an embodiment of this disclosure.

The technical solutions of the embodiments of this disclosure will be described below clearly and comprehensively in combination with the drawings of the embodiments of this disclosure. Obviously, the embodiments described are some, rather than all, of the embodiments of this disclosure. Based on the embodiments given in this disclosure, all other embodiments that would be obtained by those of ordinary skilled persons in the art without involving any inventive effort shall all fall within the scope of protection of this disclosure.

It should be understood that when used in this description and the appended claims, the terms "comprise" and "contain" indicate the presence of the described features, wholes, steps, operations, elements and/or the components, but do not exclude the presence or addition of one or more other features, wholes, steps, operations, elements, components and/or the combinations thereof.

It should also be understood that the terms used in the description of this disclosure are only intended to describe specific embodiments, but not to limit this disclosure. As used in the description and the appended claims of th this disclosure, unless the context clearly indicates otherwise, the singular forms "a", "an" and "the" are intended to comprise the plural forms.

It should also be further understood that the term "and/or" used in the description and the appended claims oft this disclosure refers to one of the items listed or any combination and all possible combinations of the items listed, and includes these combinations.

As used in the description and the appended claims, the term "if" may be interpreted as "when" or "once" or "in response to determination" or "in response to detection" according to the context. Similarly, the phrase "if determined" or "if detected [described condition or event]" may be interpreted as "once determined" or "in response to determination" or "once detected [described condition or event]" or "in response to detection of [the described condition or event]" according to the context.

In specific implementations, the terminal described in the embodiments of this disclosure includes, but is not limited to, other portable devices such as a mobile phone, a laptop computer, or a tablet computer with a touch-sensitive surface (e.g., a touch screen display and/or a touch pad). It should also be understood that, in some embodiments, the device is not a portable communication device, but a desktop computer with a touch-sensitive surface (e.g., a touch screen display and/or a touch pad).

An apparatus including a display and a touch-sensitive surface is described in the following discussion. However, it should be understood that the terminal may include one or more other physical user interface devices such as a physical keyboard, a mouse, and/or a joystick.

In the embodiments of this disclosure, an apparatus and a method for removing high-frequency radio frequency interference can be used for removing a high-frequency radio frequency interference signal from an electroencephalogram signal (EEG) collected in a medical monitoring system, where the electroencephalogram signal includes, but is not limited to, an $\alpha$ wave, a $\beta$ Wave, a $\theta$ wave and a $\delta$ wave, etc.

Refer to FIG. 1, FIG. 1 is a block diagram for an apparatus for removing high-frequency radio frequency interference provided by an embodiment of this disclosure. As shown in the figure, the apparatus may include: a filtering unit 101, a high-frequency signal extraction unit 102, a marking unit 103, a collection unit 104, and a processor 105.

The filtering unit 101 may include an input port and an output port, where its input port may be inputted with an original electroencephalogram signal. The high-frequency signal extraction unit 102 may include an input port and an output port, where its input port may be connected with the output port of the filtering unit 101. The collection unit 104 may include an input port and an output port, where its input port may be connected with the output port of the filtering unit 101. The processor 105 may include an input port and an output port, where its input port may be connected with the output port of the collection unit 104. The marking unit 103 may include an input port that may be connected with the output port of the high-frequency signal extraction unit 102 and the output port of the processor 105.

The filtering unit 101 may filter the original electroencephalogram signal to obtain an intermediate electroencephalogram signal. The high-frequency signal extraction unit 102 may filter the intermediate electroencephalogram signal to extract a high-frequency signal in the intermediate electroencephalogram signal. The marking unit 103 may compare an amplitude of the high-frequency signal with a comparison threshold value, and perform classification marking on the intermediate electroencephalogram signal when a comparison result indicates that the amplitude of the high-frequency signal is greater than the comparison threshold value. The collection unit 104 may selectively sample the intermediate electroencephalogram signal to obtain a desired electroencephalogram signal and input the desired electroencephalogram signal into the processor 105. Here, when the comparison result indicates that the amplitude of the high-frequency signal is equal to or lower than the comparison threshold value, the collection unit 104 may directly sample the intermediate electroencephalogram signal as the desired electroencephalogram signal; when the comparison result indicates that the amplitude of the high-frequency signal is greater than the comparison threshold value, the collection unit 104 may stop sampling the interfered intermediate electroencephalogram signal. The processor may set the comparison threshold value used by the marking unit 103 and control the collection unit 104 to perform sampling on the intermediate electroencephalogram signal.

In the embodiment of this disclosure, the filtering unit 101 can perform low-pass filtering on the original electroencephalogram signal inputted into the input port thereof to obtain the intermediate electroencephalogram signal after the attenuation of the signal outside the frequency band of the electroencephalogram signal. The intermediate electroencephalogram signal can be inputted into the high-frequency signal extraction unit 102 to extract the high-frequency signal therein. The high-frequency signal can be then inputted into the marking unit, and the marking unit 103 can compare the high-frequency signal with the comparison threshold value set by the processor 105. When the comparison result represents that the amplitude of the high-frequency signal is greater than the comparison threshold value, it indicates that the original electroencephalogram signal corresponding to the high-frequency signal is interfered, and the marking unit 103 may mark the intermediate electroencephalogram signal, so that the collection unit 104 can sample the desired electroencephalogram signal without the electroencephalogram signal with the interference marking.

Figure 2:
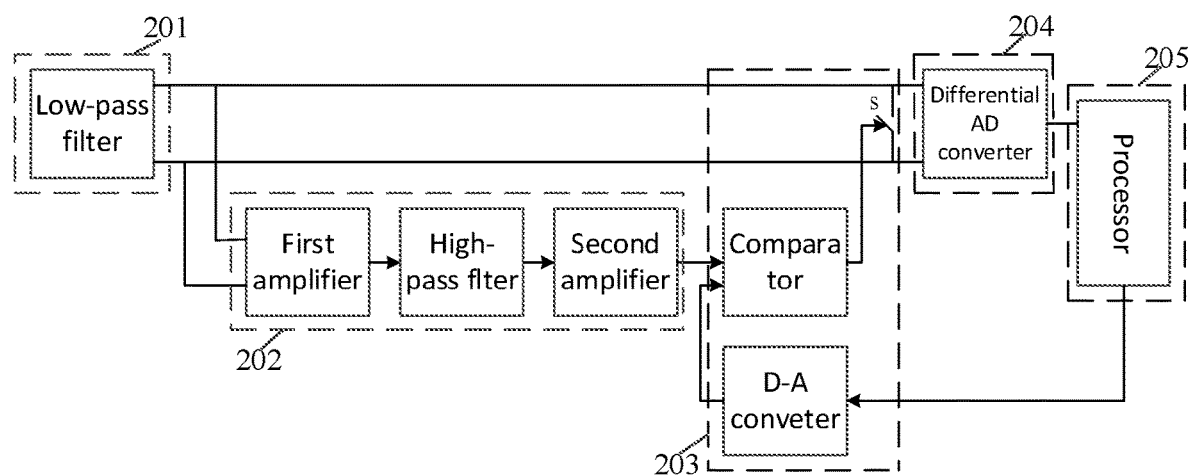
FIG. 2 is a schematic structural diagram for an apparatus for removing high-frequency radio frequency interference provided by an embodiment of this disclosure.

Refer to FIG. 2, FIG. 2 is a schematic structural diagram for an apparatus for removing high-frequency radio frequency interference provided by an embodiment of this disclosure. As shown in the figure, the apparatus may include: a filtering unit 201, a high-frequency signal extraction unit 202, a marking unit 203, a collection unit 204, and a processor 205.

The filtering unit 201 may include an input port and an output port, where its input port may be inputted with an original electroencephalogram signal. The high-frequency signal extraction unit 202 may include an input port and an output port, where its input port may be connected with the output port of the filtering unit 201. The collection unit 204 may include an input port and an output port, where its input port may be connected with the output port of the filtering unit 201. The processor 205 may include an input port and an output port, where its input port may be connected with the output port of the collection unit 204. The marking unit 203 may include an input port that may be connected with the output port of the high-frequency signal extraction unit 202 and the output port of the processor 205.

The filtering unit 201 may filter the original electroencephalogram signal to obtain an intermediate electroencephalogram signal. The high-frequency signal extraction unit 202 may filter the intermediate electroencephalogram signal to extract a high-frequency signal in the intermediate electroencephalogram signal. The marking unit 203 may compare an amplitude of the high-frequency signal with a comparison threshold value, and perform classification marking on the intermediate electroencephalogram signal when a comparison result indicates that the amplitude of the high-frequency signal is greater than the comparison threshold value. The collection unit 204 may selectively sample the intermediate electroencephalogram signal to obtain a desired electroencephalogram signal and input the desired electroencephalogram signal into the processor. The processor 205 may set the comparison threshold value used by the marking unit and control the collection unit 204 to perform sampling on the intermediate electroencephalogram signal. In some embodiments, the processor 205 may also update the comparison threshold value according to the intermediate electroencephalogram signal output by the collection unit 204, and output the updated comparison threshold value. Here, when the amplitude of the high-frequency signal is greater than the comparison threshold value, the corresponding intermediate electroencephalogram signal is indicated to be interfered, and the collection unit 204 may not sample the interfered electroencephalogram signal; when the amplitude of the high-frequency signal is lower than or equal to the comparison threshold value, the collection unit 204 may sample (e.g., directly) the intermediate electroencephalogram signal as the desired electroencephalogram signal.

The filtering unit 201 may include a low-pass filter, and the original electroencephalogram signal acquired by one or more electroencephalogram signal leads may be inputted into two input ports of the low-pass filter, where the original electroencephalogram signal can be a differential signal.

The high-frequency signal extraction unit 202 may include a first amplifier that may include two input ports and an output port, a high-pass filter that may include an input port and an output, and a second amplifier that may include an input port and an output, where the two input ports of the first amplifier may be respectively connected with two output ports of the low-pass filter, the output port of the first amplifier may be connected with the input port of the high-pass filter; and the output port of the high-pass filter may be connected with the input port of the second amplifier.

The marking unit 203 may include a single-ended digital-to-analog converter that may include an input port and an output port, a high-speed comparator that may include a first input port, a second input port and an output port, and a switch S. The input port of the single-ended digital-to-analog converter may be connected with the output port of the processor 205. The first input port of the high-speed comparator may be connected with the output port of the single-ended digital-to-analog converter, and the second input port of the high-speed comparator may be connected with the output port of the second amplifier in the high-frequency signal extraction unit 202. Both ports of the switch S may be respectively connected with the two output ports of the low-pass filter, and the switch S may be controlled to be closed and opened according to a comparison result of the high-speed comparator.

The collection unit 204 may include a differential analog-to-digital converter, where the differential analog-to-digital converter may include two input ports and an output port. The two input ports may be respectively connected with the two output ports of the low-pass filter in the filtering unit 201. Also, the two input ports of the differential analog-to-digital converter may be respectively connected with both ports of the switch S in the marking unit 203, and the output port of the differential analog-to-digital converter may be connected with the processor 205.

In the embodiment of this disclosure, the low-pass filter may perform low-pass filtering on the original electroencephalogram signal acquired by the electroencephalogram signal lead(s) to obtain the intermediate electroencephalogram signal after the attenuation of the signal outside the frequency band of the electroencephalogram signal, where the intermediate electroencephalogram signal can be a differential signal. The intermediate electroencephalogram signal may be inputted into the first amplifier, and the first amplifier may amplify the intermediate electroencephalogram signal. Since the intermediate electroencephalogram signal is a differential signal, the first amplifier may convert the intermediate electroencephalogram signal into a single-ended first intermediate electroencephalogram signal. The high-pass filter may perform high-pass filtering on the first intermediate electroencephalogram signal to extract a high-frequency signal therein. The second amplifier may amplify the high-frequency signal to increase the amplitude of the high-frequency signal, and send a second intermediate electroencephalogram signal obtained after the increase operation to the high-speed comparator in the marking unit 203. Here, the first intermediate electroencephalogram signal and the second intermediate electroencephalogram signal can both be single-ended signals. In the marking unit 203, the single-ended digital-to-analog converter may receive the comparison threshold value set by the processor, and convert the comparison threshold value into a reference voltage, where the comparison threshold value can be a constant threshold value obtained by statistical analysis of clinical experience data. The high-speed comparator may compare an amplitude of the second intermediate electroencephalogram signal inputted by the second amplifier with the reference voltage, and output the comparison result to the switch S. When the comparison result indicates that the amplitude of the high-frequency signal is greater than the reference voltage, it may indicate that the intermediate electroencephalogram signal is interfered by the high-frequency radio frequency signal, the high-speed comparator may output a high-level signal, and the switch S is closed, to achieve a short circuit between the two input ports of the differential analog-to-digital converter, so that the differential analog-to-digital converter can sample a zero signal, thereby realizing the classification marking on the interfered intermediate electroencephalogram signal. That is, when the amplitude of the high-frequency signal is greater than the reference voltage, the differential analog-to-digital converter can sample a zero signal, so that the waveform of the sampled electroencephalogram signal may exhibit a zero pulse, thereby marking the interfered intermediate electroencephalogram signal. When the comparison result indicates that the amplitude of the high-frequency signal is less than or equal to the reference voltage, it may indicate that the intermediate electroencephalogram signal is not interfered by the high-frequency radio frequency signal, the high-frequency comparator may output a low-level signal, and the switch S may be opened. In this case, the differential digital-to-analog converter may normally sample the intermediate electroencephalogram signal to obtain the desired electroencephalogram signal. As described above, the differential analog-to-digital converter can selectively sample the electroencephalogram signal by closing and opening the switch S. That is, the differential analog-to-digital converter can sample the intermediate electroencephalogram signal as the desired electroencephalogram signal when the intermediate electroencephalogram signal is not interfered, and the differential analog-to-digital converter can sample the zero signal rather than the intermediate electroencephalogram signal when the intermediate electroencephalogram signal is determined to be interfered.

Figure 3:
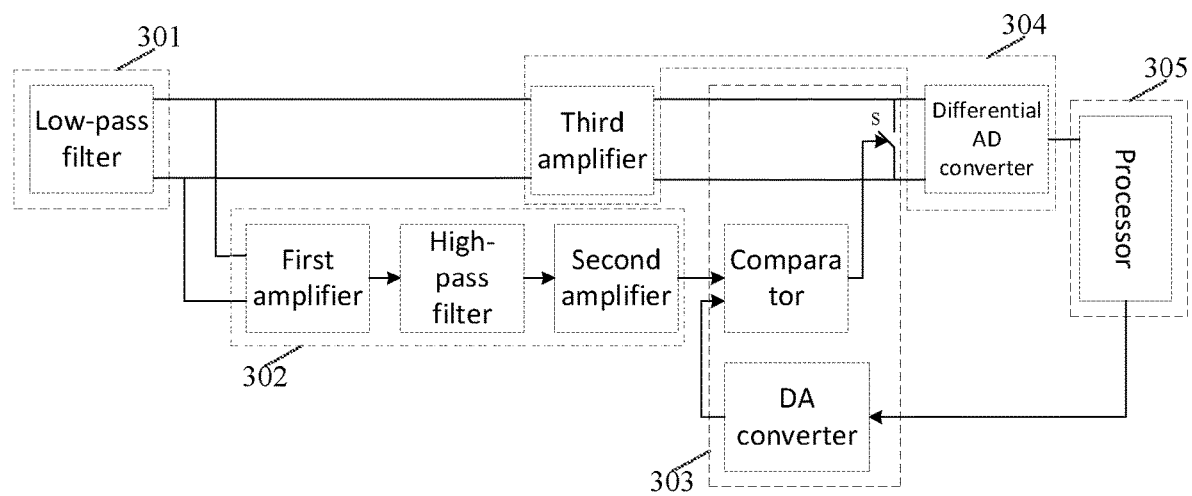
FIG. 3 is a schematic structural diagram for another apparatus for removing high-frequency radio frequency interference provided by an embodiment of this disclosure.

In some embodiments, the collection unit 204 may further include a third amplifier that may amplify the intermediate electroencephalogram signal and output a third intermediate electroencephalogram signal obtained by amplifying the intermediate electroencephalogram signal, so as to facilitate the sampling by the differential analog-to-digital converter. As shown in FIG. 3, the third amplifier may include two input ports and an output port, where the input ports of the third amplifier is connected with the output ports of the low-pass filter, and the output port of the third amplifier is connected with the input ports of the differential analog-to-digital converter.

In some embodiments, the third amplifier may either be arranged before the switch S, or after the switch S, which will not be specifically limited in the embodiments of this disclosure.

In some embodiments, the third amplifier includes, but is not limited to, a general-purpose amplifier, a high-speed amplifier, a low-power-consumption amplifier, a programmable gain amplifier (PGA), etc.

In some embodiments, the third amplifier and the differential analog-to-digital converter may be two separate devices, or may be dedicated EEG collection chips with amplifier and analog-to-digital conversion functions, which will not be specifically defined in the embodiments of this disclosure.

In some embodiments, the differential analog-to-digital converter may be any one of an 8-bit analog-to-digital converter, a 10-bit analog-to-digital converter, a 12-bit analog-to-digital converter, a 16-bit analog-to-digital converter, or a 24-bit analog-to-digital converter, which will not be specifically defined in the embodiments of this disclosure.

In some embodiments, the processor 205 may further process the electroencephalogram signal according to the respective classification mark of the electroencephalogram signal. For example, when the amplitude of the second intermediate electroencephalogram signal is greater than the reference voltage, the switch module S can be is closed to achieve a short-circuit between the two input ports of the differential analog-to-digital converter, so that the analog-to-digital converter may sample the zero signal. However, due to the presence of noise in the differential analog-to-digital converter and the apparatus for removing high-frequency radio frequency interference, the amplitude of the zero signal is not necessarily zero. Correspondingly, the processor 205 can set a zeroing threshold value so as to set the value of the electroencephalogram signal having an amplitude lower than the zeroing threshold value, which is sampled by the differential analog-to-digital converter, to be zero.

In some embodiments, the low-pass filter includes, but is not limited to, a second-order passive RC filter, a third-order passive RC filter, etc., which will not be specifically defined in the embodiments of the present invention.

It can be seen that in the embodiments of this disclosure, the high-frequency signal extraction unit in the apparatus for removing high-frequency radio frequency interference may extract the high-frequency signal in the electroencephalogram signal, and compare the high-frequency signal with the preset comparison threshold value to determine whether the high-frequency signal is an interference signal, and when it is determined that the high-frequency signal is an interference signal, the electroencephalogram signal corresponding to the interference signal is set to be zero by the marking unit, so that the interference signal in the electroencephalogram signal can be effectively removed.

Figure 4:
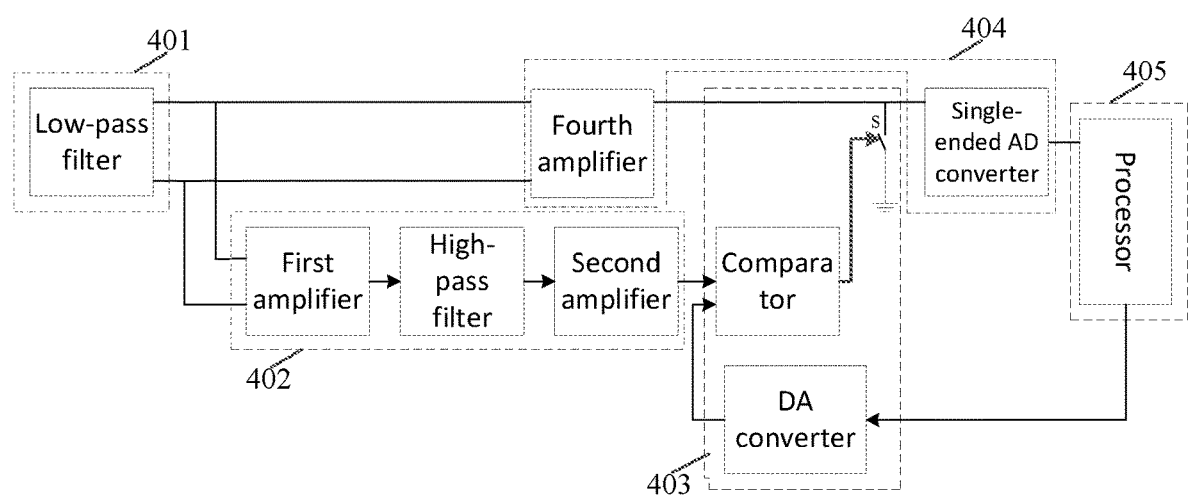
FIG. 4 is a schematic structural diagram for another apparatus for removing high-frequency radio frequency interference provided by an embodiment of this disclosure.

Referring to FIG. 4, FIG. 4 is a schematic structural diagram of another apparatus for removing high-frequency radio frequency interference provided by an embodiment of this disclosure. As shown in FIG. 4, the apparatus may include: a filtering unit 401, a high-frequency signal extraction unit 402, a marking unit 403, a collection unit 404, and a processor 405.

The filtering unit 401 may include an input port and an output port, where its input port may be inputted with an original electroencephalogram signal. The high-frequency signal extraction unit 402 may include an input port and an output port, where its input port may be connected with the output port of the filtering unit 401. The collection unit 404 may include an input port and an output port, where its input port may be connected with the output port of the filtering unit 401. The processor 405 may include an input port and an output port, where its input port may be connected with the output port of the filtering unit 401 and the output port of the collection unit 404. The marking unit 403 may include an input port that may be connected with the output port of the high-frequency signal extraction unit 402 and the output port of the processor 405.

The filtering unit 401 may filter the original electroencephalogram signal to obtain intermediate electroencephalogram signals. The high-frequency signal extraction unit 402 may filter the intermediate electroencephalogram signal to extract a high-frequency signal in the intermediate electroencephalogram signal. The marking unit 403 may compare an amplitude of the high-frequency signal with a comparison threshold value, and perform classification marking on the intermediate electroencephalogram signal when a comparison result indicates that the amplitude of the high-frequency signal is greater than the comparison threshold value. The collection unit 404 may sample a desired electroencephalogram signal and input the desired electroencephalogram signal into the processor. The processor 405 may set the comparison threshold value used by the marking unit and control the collection unit 404 to perform sampling on the intermediate electroencephalogram signal.

The filtering unit 401 may include a low-pass filter, and the original electroencephalogram signal acquired by one or more electroencephalogram signal lead(s) may be inputted into two input ports of the low-pass filter, where the original electroencephalogram signal may be a differential signal.

The high-frequency signal extraction unit 402 may include a first amplifier that may include two input ports and an output port, a high-pass filter that may include an input port and an output, and a second amplifier that may include an input port and an output, where the two input ports of the first amplifier may be respectively connected with two output ports of the low-pass filter, the output port of the first amplifier may be connected with the input port of the high-pass filter; and the output port of the high-pass filter may be connected with the input port of the second amplifier.

The marking unit 403 may include a single-ended digital-to-analog converter that may include an input port and an output port, a high-speed comparator that may include a first input port, a second input port and an output port, and a switch S. The input port of the single-ended digital-to-analog converter may be connected with the output port of the processor 405. The first input port of the high-speed comparator may be connected with the output port of the single-ended digital-to-analog converter, and the second input port of the high-speed comparator may be connected with the output port of the second amplifier in the high-frequency signal extraction unit 402. The switch S may include a first port that may be connected with the collection unit 404, and the switch S may be controlled by the processor 405 to be closed or opened according to a comparison result of the high-speed comparator.

The collection unit 404 may include a fourth amplifier that may include two input ports and an output port and a single-ended analog-to-digital converter that may include an input port and an output port. The fourth amplifier may be an instrumentation amplifier, where the two input ports of the instrumentation amplifier may be respectively connected with the output ports of the low-pass filter, and the output port of the instrumentation amplifier may be connected with the input port of the single-ended analog-to-digital converter. The output port of the single-ended analog-to-digital converter may be connected with the processor 405.

In some embodiments, the switch S may be connected before the fourth amplifier, or between the fourth amplifier and the single-ended analog-to-digital converter. If the switch S is connected before the fourth amplifier, both ends of the switch S may be respectively connected with the two input ports of the fourth amplifier; and if the switch S is connected before the single-ended analog-to-digital converter, one end of the switch S may be connected with the input port of the single-ended analog-to-digital converter, and the other port is grounded.

In the embodiment of this disclosure, the low-pass filter can perform low-pass filtering on the original electroencephalogram signal acquired by one or more electroencephalogram signal lead(s) to obtain the intermediate electroencephalogram signal after the attenuation of the signal outside the frequency band of the EEG signal, where the intermediate electroencephalogram signal can be a differential signal. The intermediate electroencephalogram signal may be inputted into the first amplifier, and the first amplifier may amplify the intermediate electroencephalogram signal. Since the intermediate electroencephalogram signal are a differential signal, the first amplifier may further convert the intermediate electroencephalogram signal into a single-ended first intermediate electroencephalogram signal. The high-pass filter may perform high-pass filtering on the first intermediate electroencephalogram signal to extract the high-frequency signal therein. The second amplifier may amplify the high-frequency signal to increase the amplitude of the high-frequency signal, and send a second intermediate electroencephalogram signal obtained after the increase operation to the high-speed comparator in the marking unit 403. In the marking unit 403, the single-ended digital-to-analog converter may receive the comparison threshold value set by the processor, and convert the comparison threshold value into a reference voltage, where the comparison threshold value can be a constant threshold value obtained by statistical analysis of clinical experience data. The high-speed comparator may compare the amplitude of the high-frequency signal inputted by the second amplifier with the reference voltage, and output the comparison result to the switch S. When the comparison result indicates that the amplitude of the high-frequency signal is greater than the reference voltage, it may indicate that the intermediate electroencephalogram signal is interfered by the high-frequency radio frequency signal, the high-speed comparator may output a high-level signal, and the switch S is closed to make the single-ended analog-to-digital converter be grounded, so that the single-ended analog-to-digital converter can sample a zero signal to realize the classification marking on the interfered intermediate electroencephalogram signal. That is, when the amplitude of the high-frequency signal is greater than the reference voltage, the single-ended analog-to-digital converter can sample a zero signal, so that the waveform of the sampled electroencephalogram signal may exhibit a zero pulse, thereby marking the interfered intermediate electroencephalogram signal. When the amplitude of the high-frequency signal is less than the reference voltage, it may indicate that the original electroencephalogram signal is not interfered by the high-frequency radio frequency signal, the high-speed comparator may output a low-level signal, and the switch S may be opened. In this case, the collection unit 404 may normally sample the intermediate electroencephalogram signal to obtain the desired electroencephalogram signal. In this case, the fourth amplifier of the collection unit 404 may further amplify the intermediate electroencephalogram signal and convert the intermediate electroencephalogram signal into a single-ended fourth intermediate electroencephalogram signal to facilitate the sampling of the single-ended analog-to-digital converter. The single-ended analog-to-digital converter may normally sample the amplified intermediate electroencephalogram signal to obtain the desired electroencephalogram signal. As described above, the single-ended analog-to-digital converter can sample the zero signal to remove the interfered electroencephalogram signal and the normal electroencephalogram signal by closing and opening the switch S.

It can be understood that there can be multiple EEG measurement channels in a medical monitoring system. Although the embodiments of this disclosure only provides the collection and processing process of one of the channels, the collection and processing of other channels can refer to the processes in the above-described embodiments, or the electroencephalogram signal in other channels can be processed in a same way as the electroencephalogram signal of the marked channel. For example, the medical monitoring system may include four EEG measurement channels including an α wave channel, a β wave channel, a θ wave channel, and a δ wave channel. The apparatus for removing high-frequency radio frequency interference can process the electroencephalogram signal in the above-mentioned four EEG channels following the embodiments for marking and sampling the electroencephalogram signal described above, or the apparatus for removing high-frequency radio frequency interference removal may only mark and sample, following the above-described embodiments, the electroencephalogram signal of the δ wave channel, and perform the same marking processing on the electroencephalogram signals of the other three channels collected at the same time as that of the δ wave channel.

It can be seen that in the embodiments of this disclosure, the high-frequency signal extraction unit in the apparatus for removing high-frequency radio frequency interference can extract the high-frequency signal from the electroencephalogram signal, and compare the high-frequency signal with the preset comparison threshold value to determine whether the high-frequency signal is an interference signal; and when it is determined that the high-frequency signal is an interference signal, the electroencephalogram signal corresponding to the interference signal can be set to zero by the marking unit, so that the interference signal in the electroencephalogram signal can be effectively removed.

Figure 5:
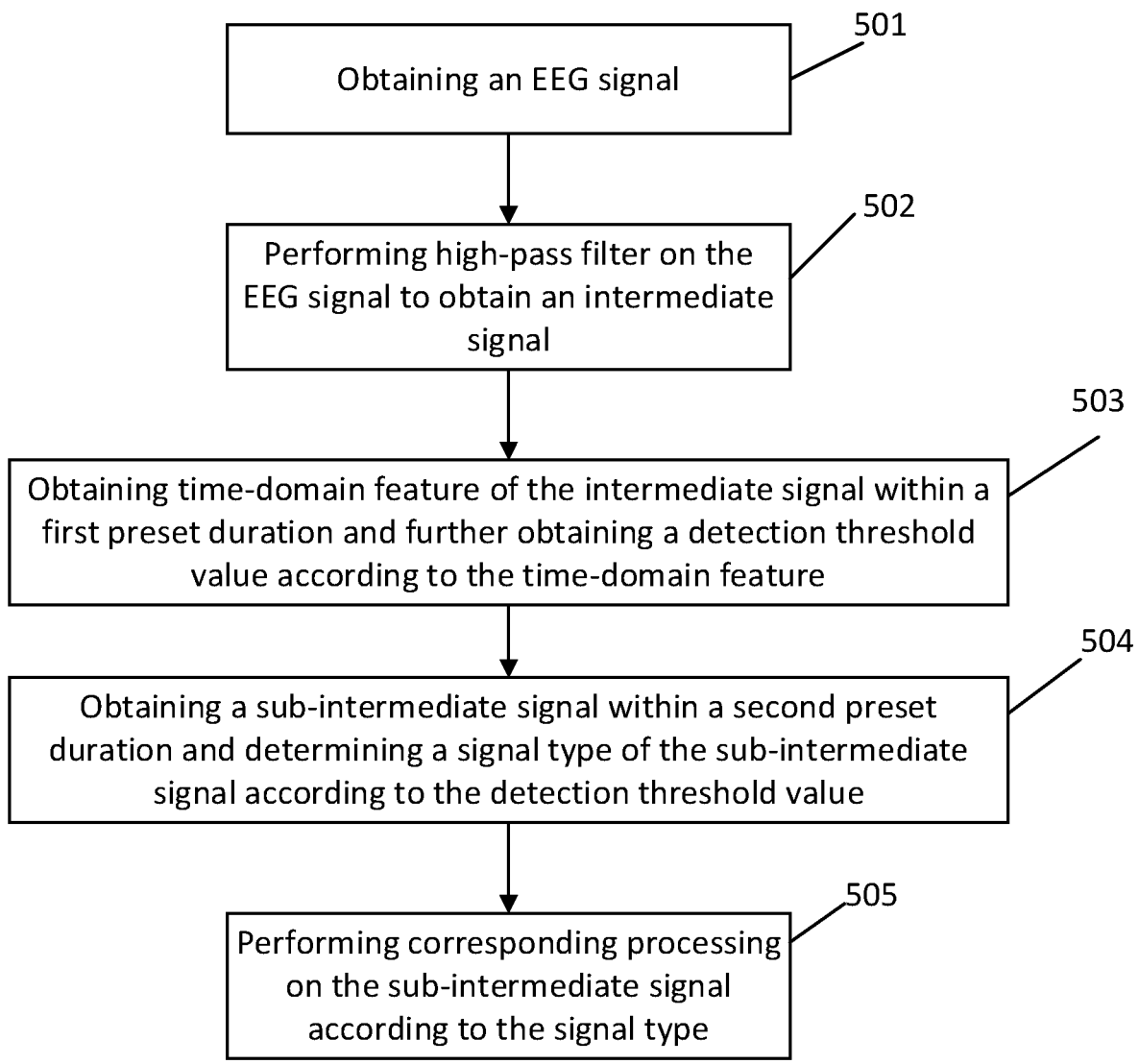
FIG. 5 is a schematic flowchart for a method for removing high-frequency radio frequency interference provided by an embodiment of this disclosure.

Referring to FIG. 5, FIG. 5 is a schematic flowchart for a method for removing high-frequency radio frequency interference provided by an embodiment of this disclosure. As shown in FIG. 5, the method comprises the following steps 501-505.

In step 501, an electroencephalogram signal may be acquired.

In the embodiment of this disclosure, the sampling frequency of the acquired electroencephalogram signal is not less than 2 kHz.

In step 502, high-pass filtering may be performed on the electroencephalogram signal to obtain an intermediate signal.

In the embodiment of this disclosure, the frequency of a normal electroencephalogram signal is less than 100 Hz, and the frequency of the high-frequency radio frequency interference signal is greater than 10 kHz. Accordingly, the high-pass filtering can attenuate a low-frequency signal in the electroencephalogram signal to obtain the intermediate signal which may mainly include the high-frequency radio frequency interference signal.

In step 503, a time-domain feature of the intermediate signal can be obtained according to a first preset duration, and a detection threshold value can be obtained according to the time-domain feature.

In the embodiment of this disclosure, the time-domain feature includes, but is not limited to, an amplitude of the intermediate signal, an average value of the amplitudes of the intermediate signal, and a variance of the amplitudes of the intermediate signal. When obtaining the detection threshold value according to the time-domain feature, taking the first preset duration is T and there are M sampling points within the first preset duration as an example, the average value of the amplitudes of the M sampling points may be taken as the detection threshold value. It should be understood that the above-mentioned examples are for illustration only and cannot be understood as specific definitions.

In step 504, a sub-intermediate signal may be obtained according to a second preset duration, and a signal type of the sub-intermediate signal can be determined according to the detection threshold value, where different signal types reflect different degrees of interference on the electroencephalogram signal.

In the embodiment of this disclosure, a segment of sub-intermediate signal with a second duration T may be acquired from the intermediate signal, and the time-domain feature of the sub-intermediate signal may be compared with the detection threshold value to determine the signal type of the sub-intermediate signal. For example, when the amplitude of the sub-intermediate signal is greater than or equal to the detection threshold value, the sub-intermediate signal may be determined to be an interference signal, and when the amplitude of the sub-intermediate signal is less than the detection threshold value, the sub-intermediate signal may be determined to be a non-interference signal. It should be understood that the above-mentioned example are for illustration only and cannot be understood as specific definitions.

In step 505, different processing may be performed, according to the determined signal type, on the electroencephalogram signal corresponding to the sub-intermediate signal.

In the embodiment of this disclosure, when the sub-intermediate signal is an interference signal, the electroencephalogram signal corresponding to this sub-intermediate signal may be a signal subjected to the high-frequency radio frequency interference, and when the sub-intermediate signal is a non-interference signal, the electroencephalogram signal corresponding to the sub-intermediate signal can be a normal signal. Here, different signal processing may be performed on the electroencephalogram signal subjected to the high-frequency radio frequency interference and the normal electroencephalogram signal. For example, when the electroencephalogram signal within a certain time period is subjected to the high-frequency radio frequency interference, the signal subjected to the high-frequency radio frequency interference may be replaced with a normal electroencephalogram signal with the same duration as the interfered signal. For example, the normal electroencephalogram signal may be selected from those signals acquired before the appearance of the interfered signal.

For example, the high-pass filtering can be performed on the sampled electroencephalogram signal to obtain the intermediate signal; a segment of intermediate signal of the first preset duration can then be acquired, and the average value of the amplitudes of the segment of intermediate signal within the first preset duration can be calculated, where the average value may be taken as the detection threshold value. After that, a segment of sub-intermediate signal of the second duration can be acquired from the intermediate signal, and the average value of the amplitudes of the sub-intermediate signal within the second preset duration may be calculated. When the average value of the amplitudes of the sub-intermediate signal within the second preset duration is greater than or equal to the detection threshold value, it can be determined that the sub-intermediate signal is an interference signal, and the electroencephalogram signal corresponding to the sub-intermediate signal is subjected to the high-frequency radio frequency interference; and when the average value of the amplitudes of the sub-intermediate signal within the second preset duration is less than the detection threshold value, it can be determined that the sub-intermediate signal is a non-interference signal, and the electroencephalogram signal corresponding to the sub-intermediate signal is a normal electroencephalogram signal. For the electroencephalogram signal subjected to the high-frequency radio frequency interference, the electroencephalogram signal corresponding to the interference signal may be replaced with the normal electroencephalogram signal with the same duration as the electroencephalogram signal subjected to the high-frequency radio frequency interference.

In some embodiments, the second preset duration T may be less than the first preset duration τ, may be equal to the first preset duration τ, or may be greater than the first preset duration τ, which will not be specifically defined in the embodiments of this disclosure.

In some embodiments, the detection threshold value calculated according to the intermediate signal of the first preset time duration may be taken as the detection threshold value of the sub-intermediate signal within the second preset duration, or may be taken as the detection threshold value of the sub-intermediate signal within the next second preset duration, or may be taken as the detection threshold value of the signal within a third preset duration, where the third preset duration may be a duration in the next segment of sub-intermediate signal, which will not be specifically defined in the embodiments of this disclosure.

Figure 6:
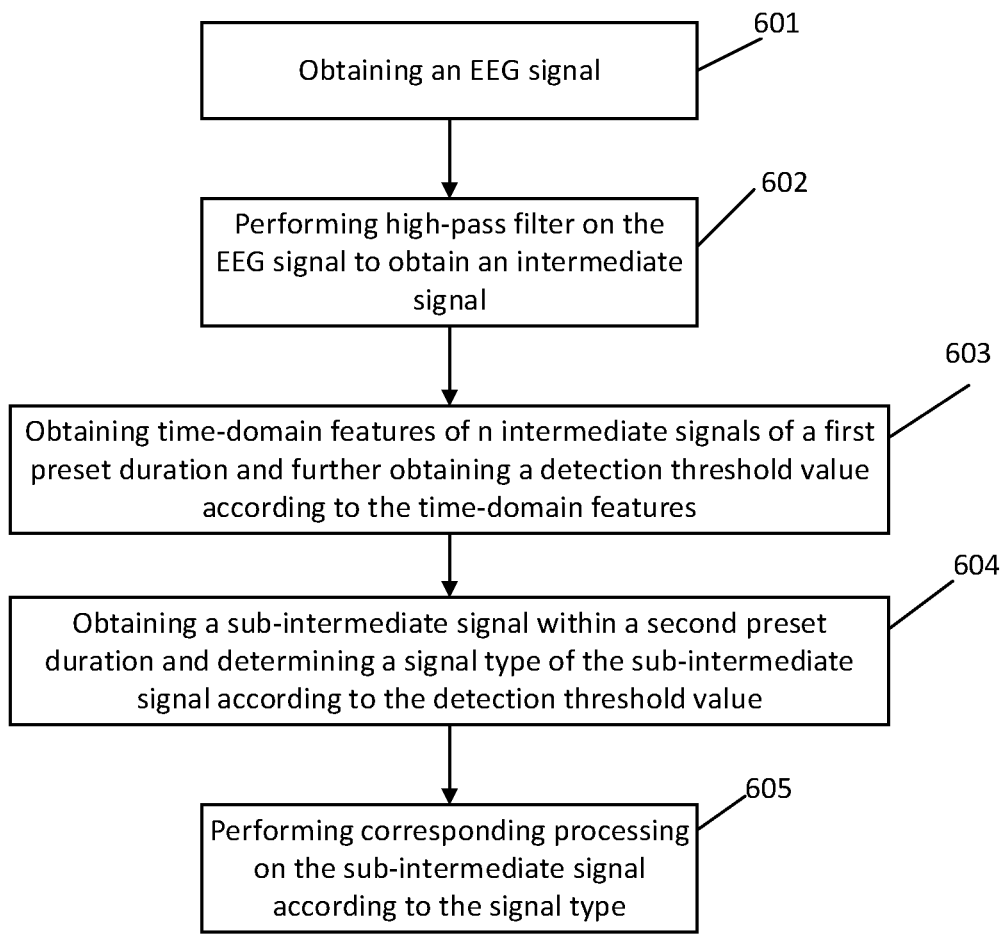
FIG. 6 is a schematic flowchart for a method for removing high-frequency radio frequency interference according to another embodiment of this disclosure.

Referring to FIG. 6, FIG. 6 is a schematic flowchart for another method for removing high-frequency radio frequency interference provided by an embodiment of this disclosure. As shown in FIG. 6, the method may include the following steps 601-605.

In step 601, an electroencephalogram signal may be acquired.

In the embodiment of this disclosure, the sampling frequency of the acquired electroencephalogram signal may be at least 2 kHz.

In step 602, high-pass filtering may be performed on the electroencephalogram signal to obtain an intermediate signal.

In the embodiment of this disclosure, the frequency of a normal electroencephalogram signal is less than 100 Hz, and the frequency of the high-frequency radio frequency interference signal is greater than 10 kHz. The low-frequency signal of the electroencephalogram signal can be attenuated by the high-pass filtering method to obtain the intermediate signal which mainly contains the high-frequency radio frequency interference signal.

In step 603, time-domain features of n intermediate signals of a first preset durations may be obtained, and a detection threshold value may be further obtained according to the time-domain features.

In the embodiment of this disclosure, the time-domain features may be envelope features of the intermediate signal, and the detection threshold value may be calculated according to the envelope features of the intermediate signal. In some embodiments, the steps of calculating the detection threshold value according to the envelope features may include the following operations.

During the first preset duration τ, the changes in the time-domain feature of an upper envelope and the time-domain feature of a lower envelope of the intermediate signal may be counted in real time, and the detection threshold value may be calculated according to the changes in the time-domain features of the upper envelope and the lower envelope. For example, n intermediate signals of the first preset durations can be acquired from the intermediate signal, an upper envelope feature and a lower envelope feature of the n intermediate signals within the first preset durations can be counted, and the detection threshold value can be calculated according to the upper envelope feature and the lower envelope feature. In some embodiments, the detection threshold value may be determined according to the following formula, $$Thd = \frac{\sum_{i=1}^{i=n\times\tau}(f_{up}(t_i) - f_{low}(t_i))}{n\times\tau} \times C$$

where C is a real number greater than 0, i and n are positive integers, τ is the first preset duration, Thd is the detection threshold value, $f_{up}(t)$ is the upper envelope feature, and $f_{low}(t)$ is the lower envelope feature.

In the embodiment of this disclosure, the upper envelope feature $f_{up}(t)$ and the lower envelope feature $f_{low}(t)$ can be obtained according to the following formulae, $$f_{up}(t)=A\times\max(x(t-\tau), \ldots, x(t))$$

$$f_{low}(t)=B\times\min(x(t-\tau), \ldots, x(t))$$

where A and B are real numbers greater than 0, and x(t) is the amplitude of the intermediate electroencephalogram signal at a time point t.

Figure 7:
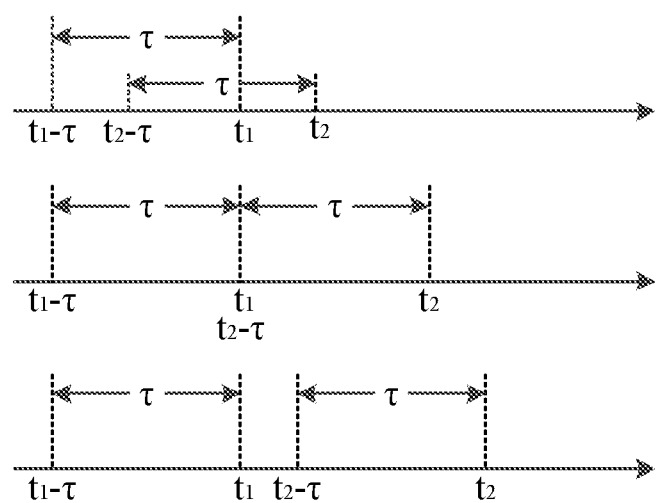
FIG. 7 is a schematic diagram of a time period relationship provided by an embodiment of this disclosure.

In the embodiment of this disclosure, when i is equal to 1, the time period corresponding to the first preset duration is from the time point $t_1-\tau$ to the time point $t_1$, and when i is equal to 2, the time period corresponding to the first preset duration is from the time point $t_2-\tau$ to the time point $t_2$. In some embodiments, as shown in FIG. 7, FIG. 7 is a schematic diagram for a time period relationship provided by an embodiment of this disclosure. The two time periods, i.e., from the time point $t_1-\tau$ to the time point $t_1$ and from the time point $t_2-\tau$ to the time point $t_2$ can contain an overlapping part, can be two consecutive time periods without overlapping, or can also be two time periods with a time interval, which will not be specifically limited in the embodiments of this disclosure.

In some embodiment, the time-domain feature is not limited to the envelope feature, where the time-domain feature may also be the average value, the variance and the standard deviation, a combination value of the average value and the maximum value or a specific value of the amplitudes of the intermediate signal, and the feature value can be the second maximum amplitude or the third maximum amplitude, which will not be specifically defined in the embodiments of this disclosure.

In step 604, a sub-intermediate signal may be obtained according to a second preset duration, and a signal type of the sub-intermediate signal can be determined according to the detection threshold value, where different signal types represent different degrees of interference on the electroencephalogram signal.

In the embodiment of this disclosure, after the detection threshold value is obtained, the signal type of the sub-intermediate signal may be determined using the following two methods.

In a first implementation, a first threshold value and a second threshold value may be obtained according to the detection threshold value, where the first threshold value may obtained by multiplying the detection threshold value by a first coefficient, the second threshold value may be obtained by multiplying the detection threshold value by a second coefficient, and the first coefficient can be greater than the second coefficient. Or, the first threshold value may be obtained by adding a first constant to the detection threshold value, the second threshold value may be obtained by adding a second constant to the detection threshold value, and the first constant can be greater than the second constant. It should be understood that the above-mentioned two methods for obtaining the first threshold value and the second threshold value are for illustration only and cannot be understood as specific definitions.

When the first threshold value is obtained by multiplying the detection threshold value by the first coefficient, and the second threshold value is obtained by multiplying the detection threshold value by the second coefficient, a segment of sub-intermediate signal of a second preset duration T can be acquired from the intermediate signal. When the amplitude of the sub-intermediate signal is greater than or equal to the first threshold value, it is determined that the sub-intermediate signal is an interference signal; when the amplitude of the sub-intermediate signal is less than the first threshold value and greater than or equal to the second threshold value, it is determined that the sub-intermediate signal is a possible interference signal; and when the amplitude of the sub-intermediate signal is less than the second threshold value, it is determined that the sub-intermediate signal is a non-interference signal.

In a second implementation, a sub-intermediate signal of a second preset duration T can be acquired from the intermediate signal, and the proportion of the amplitude of the sub-intermediate signal, which amplitude is greater than the detection threshold value, within the second preset duration can be determined. Here, when the proportion is greater than or equal to a first threshold value, it is determined that the sub-intermediate signal is an interference signal; when the proportion is smaller than the first threshold value and greater than or equal to a second threshold value, the sub-intermediate signal is determined to be a possible interference signal; and when the proportion is smaller than the second threshold value, it is determined that the sub-intermediate signal is a non-interference signal.

In some embodiments, the time period corresponding to the second preset duration T may be completely the same as, or may only partially overlap with, the time period corresponding to n first preset durations $\tau$. Alternatively, the time period corresponding to the second preset duration T may not overlap with the time period corresponding to the n first preset durations $\tau$; that is, the time period corresponding to the second preset duration T is a time period after the time period corresponding to the n first preset durations $\tau$.

In step 605, corresponding processing may be performed, according to the determined signal type of the sub-intermediate signal, on the electroencephalogram signal corresponding to the sub-intermediate signal.

In the embodiment of this disclosure, when the sub-intermediate signal is an interference signal, the electroencephalogram signal corresponding to the sub-intermediate signal is subjected to the high-frequency radio frequency interference, and the electroencephalogram signal subjected to the high-frequency radio frequency interference may be deleted, or the interfered signal may be replaced with a normal electroencephalogram signal with the same duration as the electroencephalogram signal subjected to the high-frequency radio frequency interference. When the sub-intermediate signal is a possible interference signal, the corresponding electroencephalogram signal may be a possible interfered electroencephalogram signal, and the possible interfered electroencephalogram signal may be outputted accompanying with a prompt message indicating that the possible interfered electroencephalogram signal is not reliable; or, the interfered signal may be replaced with a non-interference signal with the same duration as the possible interfered electroencephalogram signal, or the possible interfered electroencephalogram signal may be weakened. When the sub-intermediate signal is a non-interference signal, the corresponding electroencephalogram signal is a normal electroencephalogram signal, and the normal electroencephalogram signal can be outputted.

In some embodiments, the method for weakening the possible interference signal may be to replace the parameter of the segment with the parameter calculated based on the normal electroencephalogram signal before or after the appearance of the possible interfered electroencephalogram signal, or to replace the parameter of the segment with the average value of the corresponding parameters of the previous five normal electroencephalogram signals, which will not be specifically defined in the embodiments of this disclosure.

The methods for removing high-frequency radio frequency interference provided by the embodiment of this disclosure, can obtain the detection threshold value of the high-frequency radio frequency interference signal by analyzing the electroencephalogram signal in the time domain, classify the high-frequency radio frequency interference signal according to the detection threshold value, and perform the classification marking on the electroencephalogram signal according to the type of the high-frequency radio frequency interference signal, so that the electroencephalogram signal with different interference types can be processed differently.

An embodiment of this disclosure may further provide an apparatus for removing high-frequency radio frequency interference that can implement any one of the aforesaid methods. In one embodiment, the apparatus can include a collection circuit and a processor.

The collection circuit may collect an electroencephalogram signal. Specifically, the sampling frequency of the electroencephalogram signal is no less than 2 kHz.

The processor may perform high-pass filtering on the electroencephalogram signal to obtain an intermediate electroencephalogram signal. The processor may obtain a time-domain feature of the intermediate signal according to a first preset duration, and obtain a detection threshold value according to the time-domain feature. The processor may further obtain a second electroencephalogram signal according to a second preset duration, and determine a signal type of the sub-electroencephalogram signal according to the detection threshold value, where different signal types represent different degrees of interference on the electroencephalogram signal. The processor may perform, according to the determined signal type, corresponding processing on the electroencephalogram signal.

In another embodiment of this disclosure, a computer-readable storage medium may be provided, and the computer-readable storage medium may store a computer program that includes a program instruction. When the program instruction is executed by a process or, the above-described method can be achieved.

The computer-readable storage medium may be an internal storage unit of the apparatus described in any of the aforesaid embodiments, such as a hard disk or a memory of the apparatus. The computer-readable storage medium may also be an external storage device of the apparatus, such as a removable hard disk, a smart media card (SMC), a secure digital (SD) card, or a flash card equipped on the apparatus. Further, the computer-readable storage medium may further include both an internal storage unit and an external storage device of the apparatus. The computer-readable storage medium is used to store a computer program, and other programs and data required by the apparatus. The computer-readable storage medium may also be used to temporarily store data that has been or will be output.

Those of ordinary skill in the art may realize that the units and algorithm steps of various example described in combination with the embodiments disclosed in the herein can be implemented in electronic hardware, computer software or a combination of both. In order to clearly illustrate hardware and software interchangeability, the compositions and steps of the various examples have been generally described in terms of function in the above description. Whether these functions are performed in hardware or software depends on the specific application and design constraints of the technical solution. Those skilled in the art could use different methods to implement the described functions for each particular application, but such implementation should not be considered to be beyond the scope of the present invention.

Those skilled in the art would have clearly understood that for convenience and conciseness of description, the specific working processes of the above-described apparatuses can refer to the corresponding processes in the aforesaid embodiments of the method and will not be further described here.

In several embodiments provided in this application, it is to be understood that the disclosed apparatuses and methods may be implemented in other ways. For example, the apparatus embodiments described above are merely exemplary. For example, the division of the units is only a logic function division. In actual implementation, there may be other division methods, for example, multiple units or components may be combined or integrated into another system, or some features may be omitted or not implemented. In addition, the mutual coupling or direct coupling or communication connection shown or discussed may be indirect coupling or communication connection through some interfaces, apparatus or units, and may be in electrical, mechanical or other forms.

The units described as separate parts may or may not be physically separated, and the parts displayed as units may or may not be physical units, i.e., may be located in one place or may be distributed over multiple network units. Some or all of the units can be selected according to actual needs to achieve the purpose of solutions of the embodiments of the present invention.

In addition, the functional units in the embodiments of the present invention may be integrated into one processing unit or may alternatively exist as being physically separate, or two or more of the units may be integrated into one unit. The above integrated unit can be implemented in the form of hardware or a software function unit.

If the integrated unit is implemented in the form of a software function unit and sold or used as an independent product, it may be stored in a computer-readable storage medium. Based on such an understanding, the technical solutions of the present invention essentially, or the part contributing to the prior art may be implemented in the form of a software product. The computer software product may be stored in a storage medium and comprises several instructions for instructing a computer device (which may be a personal computer, a server, or a network device) to perform all or some of the steps of the methods described in the embodiments of the present invention. The aforesaid storage medium comprises: a U disk, a removable hard disk, read-only memory (ROM), a random access memory (RAM), a magnetic disk or an optical disk and other media that can store program codes.

The above description are merely the specific embodiments of the present invention, but the scope of protection of the present invention is not limited thereto, those skilled in the art would readily think of various equivalent modifications or substitutions within the technical scope disclosed in the present invention, and these modifications or substitutions should all be intended to be included within the scope of protection of the present invention. Therefore, the scope of protection of the present invention shall be subject to the scope of protection of the claims.

What is claimed is:

1. A method for removing high-frequency radio frequency interference, comprising:
   acquiring an electroencephalogram signal;
   performing high-pass filtering on the electroencephalogram signal to obtain an intermediate signal;
   obtaining a time-domain feature of the intermediate signal within a first preset duration, and calculating a detection threshold value according to the time-domain feature;
   obtaining a sub-intermediate signal within a second preset duration, and determining a signal type of the sub-intermediate signal according to the detection threshold value, wherein the signal type is determined among different signal types reflecting at least three different degrees of interference on the electroencephalogram signal; and
   performing, according to the determined signal type, corresponding processing on the electroencephalogram signal corresponding to the sub-intermediate signal.

2. The method of claim 1, wherein the time-domain feature is an envelope feature of the intermediate signal.

3. The method of claim 2, wherein calculating a detection threshold value according to the time-domain feature comprises:
   adaptively adjusting the detection threshold value according to the envelope feature.

4. The method of claim 1, wherein determining the signal type of the sub-intermediate signal according to the detection threshold value comprises:
   obtaining a first threshold value and a second threshold value according to the corresponding detection threshold value;
   when an amplitude of the sub-intermediate signal is greater than or equal to the first threshold value, determining that the sub-intermediate signal is an interference signal;
   when an amplitude of the sub-intermediate signal is less than the first threshold value and greater than or equal to the second threshold value, determining that the sub-intermediate signal is a possible interference signal; and when an amplitude of the sub-intermediate signal is less than the second threshold value, determining that the sub-intermediate signal is a non-interference signal.

5. The method of claim 4, wherein the first threshold value is obtained by multiplying the detection threshold value by a first coefficient, and the second threshold value is obtained by multiplying the detection threshold value by a second coefficient, the first coefficient being greater than the second coefficient.

6. The method of claim 4, wherein the amplitude of the sub-intermediate signal is an average value, a maximum value, a combination of the average value and the maximum value, or a specific value of amplitudes of the intermediate signal within the second preset duration.

7. The method of claim 1, wherein determining the signal type of the sub-intermediate signal according to the detection threshold value comprises:
  determining a proportion of the sub-intermediate signal, which has an amplitude greater than the detection threshold value, within the second preset duration;
  when the proportion is greater than or equal to a first threshold value, determining that the sub-intermediate signal is an interference signal;
  when the proportion is smaller than the first threshold value and is greater than or equal to a second threshold value, determining that the sub-intermediate signal is a possible interference signal; and
  when the proportion is smaller than the second threshold value, determining that the sub-intermediate signal is a non-interference signal.

8. The method of claim 1, wherein performing, according to the determined signal type, corresponding processing on the electroencephalogram signal corresponding to the sub-intermediate signal comprises:
  when the sub-intermediate signal is an interference signal, deleting the electroencephalogram signal corresponding to the sub-intermediate signal, or replacing the electroencephalogram signal corresponding to the interference signal with a normal electroencephalogram signal;
  when the sub-intermediate signal is a possible interference signal, outputting the electroencephalogram signal corresponding to the possible interference signal, and outputting a prompt message indicating that the electroencephalogram signal is not reliable, or, replacing the electroencephalogram signal corresponding to the possible interference signal with a normal electroencephalogram signal; or, weakening the electroencephalogram signal corresponding to the possible interference signal, and
  when the sub-intermediate signal is a non-interference signal, outputting the electroencephalogram signal corresponding to the non-interference signal.

9. An apparatus for removing high-frequency radio frequency interference, comprising:
  a collection circuit that collects an electroencephalogram signal; and
  a processor configured to:
  perform high-pass filtering on the electroencephalogram signal to obtain an intermediate signal;
  obtain a time-domain feature of the intermediate signal within a first preset duration, and calculate a detection threshold value according to the time-domain feature;
  obtain a sub-intermediate signal within a second preset duration, and determine a signal type of the sub-intermediate signal according to the detection threshold value, wherein the signal type is determined among different signal types reflecting at least three different degrees of interference on the electroencephalogram signal; and
  perform, according to the determined signal type, corresponding processing on the electroencephalogram signal corresponding to the sub-intermediate signal.

10. The apparatus of claim 9, wherein the processor is further configured to:
  obtain a first threshold value and a second threshold value according to the corresponding detection threshold value;
  when an amplitude of the sub-intermediate signal is greater than or equal to the first threshold value, determine that the sub-intermediate signal is an interference signal;
  if the amplitude of the sub-intermediate signal is less than the first threshold value and greater than or equal to the second threshold value, determine that the sub-intermediate signal is a possible interference signal; and
  if the amplitude of the sub-intermediate signal is less than the second threshold value, determine that the sub-intermediate signal is a non-interference signal.

11. The apparatus of claim 9, wherein to determine the signal type of the sub-intermediate signal according to the detection threshold value, the processor is configured to:
  determine a proportion of the sub-intermediate signal, which have an amplitude greater than the detection threshold value, within the second preset duration;
  when the proportion is greater than or equal to a first threshold value, determine that the sub-intermediate signal is an interference signal;
  when the proportion is smaller than the first threshold value and is greater than or equal to a second threshold value, determine that the sub-intermediate signal is a possible interference signal; and
  when the proportion is smaller than the second threshold value, determine that the sub-intermediate signal is a non-interference signal.

* * * * *